United States Patent [19]

Husband et al.

[11] Patent Number: 5,038,295

[45] Date of Patent: Aug. 6, 1991

[54] SOLID PROPELLANT SERVICE LIFE ANALYSIS VIA NONDESTRUCTIVE TESTING

[75] Inventors: David M. Husband, Tehachapi; Francisco Q. Roberto, Lancaster, both of Calif.

[73] Assignee: The United States of America as represented by the secretary of the Air Force, Washington, D.C.

[21] Appl. No.: 458,057

[22] Filed: Dec. 28, 1989

[51] Int. Cl.$^5$ ............... G01M 7/00; D03D 23/00; G01B 5/30; F02K 9/00
[52] U.S. Cl. ................. 364/508; 364/496; 364/571.03; 149/108.8; 73/760; 60/253
[58] Field of Search ............ 364/550, 496, 571.03, 364/506–508; 149/19.9, 108.8; 73/86, 87, 116, 760; 60/253

[56] References Cited

U.S. PATENT DOCUMENTS

| 4,074,563 | 2/1978 | Briar et al. | 73/35 |
| 4,090,893 | 5/1978 | Cucksee et al. | 149/19.9 |
| 4,167,428 | 9/1979 | Sayles | 149/19.9 X |
| 4,170,875 | 10/1979 | Edwards | 60/253 |

Primary Examiner—Parshotam S. Lall
Assistant Examiner—Edward Pipala
Attorney, Agent, or Firm—William G. Auton; Donald J. Singer

[57] ABSTRACT

A process for determining the aging characteristics of solid rocket propellant samples by measuring their dynamic mechanical properties is disclosed. Samples of rocket propellant are tested using a mechanical spectrometer at low strain levels and low frequencies. Since the dynamic storage modulus of a sample increases with aging time and aging temperature, it is an indicator of the acceptability of the propellant sample as a usable fuel source. The process allows a user to determine empirically the aging rate of a sample for each aging temperature with a nondestructive test procedure.

12 Claims, 6 Drawing Sheets

SOLID PROPELLANT SERVICE LIFE ANALYSIS VIA NONDESTRUCTIVE TESTING

STATEMENT OF GOVERNMENT INTEREST

The invention described herein may be manufactured and used by or for the Government for governmental purposes without the payment of any royalty thereon.

BACKGROUND OF THE INVENTION

The present invention relates generally to the fabrication of solid rocket propellants, and more specifically the invention pertains to a new technique for assessing the service life of a solid rocket propellant which allows one to characterize and analyze propellant behavior using very small samples which are nondestructively tested by dynamic mechanical measurements.

There is currently need for support devices capable of sensing the dynamic properties of propellant masses over long time periods without disturbing the integrity of the propellant charge. Should the properties of the propellant mass change significantly, then the operational capability of the rocket motor might be impaired.

Accelerated aging programs are a common method of evaluating the age stability of solid rocket propellants. Typically, ½-gallon cartons of propellant are aged at high temperatures, and during the aging period, the mechanical properties are measured by conducting tensile tests on slab samples cut from the cartons. The rate of change of a mechanical property parameter of interest (such as modulus) is then determined for each temperature. Usually an attempt is made to fit the aging rates to an Arrhenius model equation:

$$k = A \exp(-\Delta H/RT) \quad (1)$$

where
- k = aging rate constant (slope of the mechanical vs. time curve)
- ΔH = activation energy
- R = gas constant
- T = absolute temperature If the data fit such an equation (and a plot of log k vs. 1/T is linear), then the mechanical property degradation can be considered to be due to a single mechanism that is dominant up to the highest aging temperature. In this case, it is possible to calculate the change in the mechanical property parameter of interest under any aging condition. Thus, one can estimate the service life of the propellant for any temperature history. Of course, it is inadvisable to extrapolate the Arrhenius plot to higher temperatures than those used in the aging program.

In many cases, the aging data does not fit a simple Arrhenius model. If the log k vs. 1/T curve is not linear, then it is not possible to predict long-time ambient aging affects based on short-time thermally accelerated aging data. Such predictions are usually far too conservative, predicting much too short a service life for a system aged at ambient temperature.

The task Of assessing the service life of solid rocket propellant by nondestructive testing using dynamic mechanical measurement of very small samples conducted at small strain levels is alleviated, to some extent, by the systems disclosed in the following U.S. Patents, the disclosures of which are specifically incorporated herein by reference:

U.S. Pat. No. 4,170,875 issued to Edwards; and
U.S. Pat. No. 4,074,563 issued to Briar et al.

The Briar et al '563 patent discloses a dynamic sensor which is embedded within a propellant to sense and transmit information relating to dynamic modulus. The invention was devised to monitor the propellant mass as it stands, while encased within the rocket motor, so that a nondestructive assessment of the propellant properties might be determined. The Edwards '875 patent relates to a caseless rocket design which facilitates nondestructive testing.

While the above-cited references are instructive, a need remains to assess the service life of solid rocket propellants using motor samples as well as samples subjected to accelerated aging. The present invention is intended to satisfy that need.

SUMMARY OF THE INVENTION

The present invention includes a technique for assessing the service life of solid rocket propellant which allows one to characterize and analyze propellant aging behavior using very small samples which are nondestructively tested by dynamic mechanical measurements. The method can be conducted using any laboratory instrument capable of measuring dynamic mechanical properties of elastomeric materials. Test specimens are not limited in geometrical configuration; a number of different geometries can be used with this technique. Propellant samples are prepared in the desired geometrical configuration, e.g. cylindrical, rectangular, disc shaped, etc., and affixed between upper and lower test fixtures between jaws of parallel plates. The samples are then subjected to small strain dynamic mechanical analysis, and the viscoelastic properties (storage and loss moduli, compliances, tan delta, complex viscosity, etc.) are measured over a range of frequencies, and if desired, a range of temperatures. A low strain level (on the order of 1%) is selected to ensure that the tests are nondestructive and the samples can be tested repeatedly throughout the entire aging program. A series of test specimens is aged under controlled temperature and humidity conditions. The mechanical properties of the samples are measured as a function of aging time and aging temperature. A specific measurable parameter (such as complex modulus) is used to determine the overall aging behavior and service life of the propellant.

The technique of the present invention includes the accelerated aging of propellant samples by storage at elevated temperature. Service life assessment is made by determining aging rates and activation energies based on the mechanical property degradation of the samples with time over a range of temperatures. The way in which the developed technique differs from traditional methods is that the samples are tested nondestructively, and are tested repeatedly at intervals throughout the aging period. In traditional aging programs samples are tested to failure, so a large amount of material is required for a complete characterization. The techniques described in this invention require much fewer samples, much less storage space, and reduced overall handling costs. In addition, samples which have been excised directly from live solid rocket motors can be tested.

The technique was developed during a 9-month service life analysis of the propellant in the Maneuver Propulsion Assembly (MPA) motors. Propellant samples which had been excised directly from MPA motors were aged over a range of temperatures and dynamic mechanical properties were periodically measured. In addition, rectangular propellant samples cut from a slab were subjected to an identical aging analysis, and it was found that the aging modulus (G') changes with aging time for motor samples aged at temperatures from 90° to 165° F. An increase in modulus indicates that the material is becoming stiffer, or more brittle. Storage modulus vs. aging time for the rectangular propellant samples are measured. An Arrhenius analysis of the data confirms that the aging behavior of the rectangular specimens is comparable to that of the samples excised directly from the motor. The rate of aging as a function of temperature for the motor samples is determined so that the aging behavior of the propellant can be determined for any given temperature history between ambient and 165° F. A similar determination of aging behavior using traditional techniques would have required a much larger number of samples, and it would not have been possible to use samples excised directly from the rocket motors.

It is an object of the present invention to provide a nondestructive method of testing samples of solid rocket propellant which are excised directly from solid rocket motors.

It is another object of the present invention to assess the aging behavior of solid rocket propellant samples by repeatedly measuring their dynamic mechanical properties as they experience accelerated aging conditions.

These objects together with other objects, features and advantages of the invention will become more readily apparent from the following detailed description when taken in conjunction with the accompanying drawing wherein like elements are given like reference numerals throughout.

DETAILED DESCRIPTION OF THE PREFERRED EMBODIMENT

The present invention includes a new technique for assessing the service life of solid rocket propellant which allows one to characterize and analyze propellant behavior using very small samples which are nondestructively tested by dynamic mechanical measurements. The technique is advantageous in several respects: 1) because the tests are nondestructive and use small test specimens, an entire aging program can be conducted using much less propellant than is required in traditional aging programs (propellant requirements are reduced by more than an order of magnitude); 2) the technique can be applied to samples with unusual or unique geometries which cannot be tested using traditional methods; 3) test specimens can be obtained directly from live, operational, solid rocket motors, and service life and mechanical property degradation can be determined.

Figure 1:
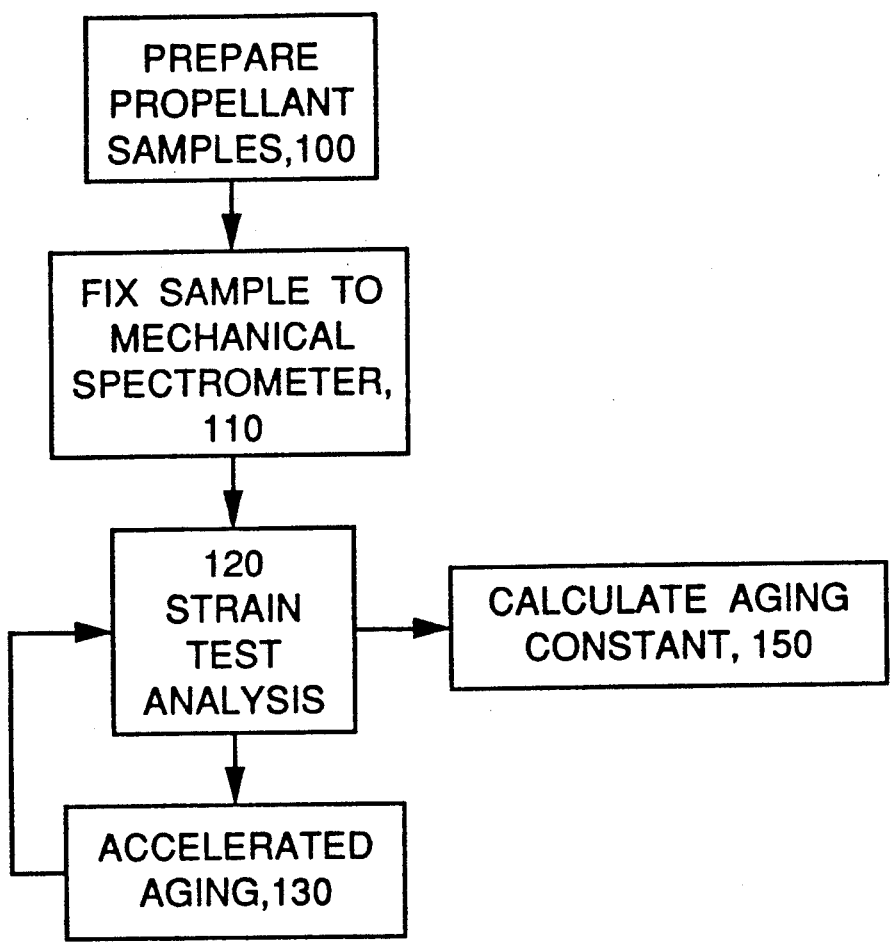
FIG. 1 is a block diagram of the steps of the process of the present invention.

The reader's attention is now directed towards FIG. 1, which is a block diagram of the steps of the process of the present invention. This process begins as propellant samples are prepared 100 in geometric sample configurations that can include: cylindrical, rectangular, square and disk shaped samples of solid rocket propellant.

In one application of the invention, the dynamic mechanical properties of the TVOPA-(1,2,3-Tris 1,2-Bis (Difluoramine Ethoxy) Propane) based propellant from Maneuver Propulsion Assembly (MPA) motors were evaluated under accelerated aging conditions using the Rheometrics mechanical spectrometer (RMS). The RMS has the capability to determine mechanical properties of a very small sample of material, allowing the evaluation of propellant samples obtained directly from motors, as well as rectangular slab samples. Samples were obtained directly from motors using a technique that included cutting the titanium (graphite overlaid) case and pushing the propellant out of the tube.

The test specimens obtained from the motors were perforated cylinders 0.50 inch outside diameter, 0.10 inch web thickness and 0.75 to 1.0 inch in length. The rectangular samples were 0.5 inch wide, 0.25 inch thick, and 1 to 2 inches in length. They were evaluated many times due to the nondestructive nature of the RMS test methods. The samples were aged for over 200 days at temperatures from 77° F. to 165° F. The dynamic mechanical properties were measured periodically at frequencies from 0.100 to 100 rad/s and at low strain rates. The dynamic moduli (G' and G") increased with time and with rising aging temperature. A rising modulus indicates that the propellant is becoming more brittle or glasslike. For most solid rocket motor applications, an increase in the propellant modulus by a factor of two to three would result in the end of the motor's useful service life.

The purpose of the present invention is to assess the service life of a solid rocket propellant by assessing its mechanical properties. These properties can include, but are not limited to: the storage and loss moduli and compliance, tan delta, and complex viscosity.

In accordance with this invention the selection of a satisfactory propellant may be made by performing an analysis of the composition's mechanical properties by use of a readily available analytical instrument for characterizing viscoelastic materials; namely, a thermomechanical spectrometer. Basically, this instrument is designed to impose on the sample being tested a selected strain which varies with the sample in a known manner, e.g., sinusoidally. The stress function related to this strain is sensed by the instrument and the stress-strain relationships are interpreted by an integral microprocessor and reported graphically as such functions as the storage modulus, the loss modulus, and the ratio of the two moduli, known as the tan delta. Accordingly, the parameters generated by the thermomechanical spectrometer describe the stress-strain properties of a given material under dynamic conditions.

Propellant samples are subjected to thermomechanical spectrometer analysis by use of a spectrometer manufactured by Rheometrics, Inc., of Piscataway, NJ. The geometric mode chosen for these tests is parallel plates and the oscillation frequency is chosen to be 1.0 radians per second. The results of the rheological analysis are set out below. This analysis is similar to that conducted by Chen et al on adhesives, as documented in U.S. Pat. No. 4,460,364 the disclosure of which is specifically incorporated herein by reference.

It should be understood that the above-set-out parameters are defined in terms of the mechanical spectrometer test analysis conducted under the conditions hereinafter set out.

Figure 2:
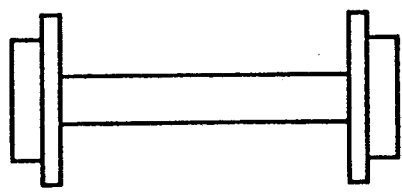
FIG. 2 is an illustration which depicts a test sample fixed between parallel plates of a mechanical spectrometer.

In the next step of the process, test specimens are attached 110 to the fixtures of the mechanical spectrometer as depicted in FIG. 2. The three types of test specimens which we have used are: a) cylindrical specimen, bonded to disposable plates; b) disk specimen, bonded to disposable plates; and c) rectangular specimen affixed between tooling jaws. In the MPA propellant service life program, cylindrical specimens were obtained by cutting MPA rockets and pushing the propellant out of the tubes. These specimens were perforated cylinders 0.50 inch outside diameter, 0.10 inch web thickness, and 0.75 to 1.0 inch in length. Rectangular samples were cut from propellant slabs and were 0.25 inch thick, 0.5 inch wide and 1-2 inches in length. In the later programs a length of 2.35 inches was used as the standard for the rectangular samples. In one embodiment of the process, the perforated cylinder samples were glued to parallel plates using a Hardman, Inc., polyurethane resin and tested in the parallel plate mode of the RMS. The rectangular samples were tested in the torsion rectangular mode of the RMS. In both cases, the specimens were strained torsionally about their length in step 120.

In the third step of the process 120, the samples are subjected repeatedly to analysis by the RMS while being subjected to: small strains, temperature variation, and aging.

Samples were aged for over 200 days at temperatures ranging from 77° F. to 165° F. The test matrix is shown in Table I. At least two motor samples were aged at each temperature from 90° F. to 165° F., and rectangular samples were aged at 77° F., 105° F., 145° F., 155° F., and 165° F. The dynamic mechanical properties of the samples were periodically measured during the aging period by subjecting the samples to oscillatory shear frequencies from 0.100 to 100 rad/sec and low strain rates. For the motor samples, a strain of 1% was selected to ensure that testing did not damage the material. The rectangular samples could sustain higher strains without damage and were thus subjected to 4% strain, producing a torque comparable to that of the cylindrical samples.

TABLE I

| SAMPLE TEST MATRIX | | | | | | | |
|---|---|---|---|---|---|---|---|
| Aging Temperature (°F.) | 77 | 90 | 105 | 125 | 145 | 155 | 165 |
| Motor Sample Numbers | 5,9,14 | 12,15,18 | 13,16,19 | 3,7 | 1,2 | 4,8 | |
| Rectangular Sample Numbers | 5 | | 7 | | 3 | 2 | 6 |

The viscoelastic response of the material undergoing oscillation was measured by the RMS. The mechanical properties of interest are G′, the dynamic storage modulus, and G″, the dynamic loss modulus. The storage modulus (which is a shear property) can be related to a tensile property (the initial modulus, $E_o$) which is measured in tensile tests by the relationship $G' = \frac{1}{3} E_o$. The ratio G″/G′ is defined as tan delta, the ratio of energy lost to energy stored during the deformation. Tan delta can also be considered as the ratio of the material's viscous-to-elastic components. Finally, the complex viscosity, $\eta^*$, is a function of G′ and G″ and is related to the energy required to deform the material.

While the process of the present invention has been described in terms of evaluating TVOPA-(1, 2, 3-Tris 1, 2-Bis (Difluoramine Ethoxy) Propane), this process can be used to assess the service life of any solid rocket propellant, by continuously evaluating its dynamic mechanical properties. Accelerated aging of the propellant is performed by exposing the fuel to selected temperatures, since the aging rate of many propellants is temperature dependent. This step 130 in FIG. 1 was performed as samples were aged 200 days at temperatures ranging between 75°–165° F.

The mechanical spectrometer repeatedly measures the dynamic mechanical properties of the sample propellant in step 120 (such as the storage modulus) which indicates the chemical decomposition of the fuel. More specifically, the storage modulus is known to increase with age.

In step 120 of FIG. 1 the samples are subjected to strain levels ranging between 1 and 4 percent. The term "strain" is a dimensionless term and refers to the ratio of the amount of torsion the sample experiences divided by its original width, when the strain is shear. For tensile strain, the ratio is produced by the amount of elongation the sample experiences divided by its original length. In most tests of the sample, strain is applied as the fixtures of the mechanical spectrometer twist the sample with a strain ranging between 0.01 and 0.04 at frequencies which may range between 1-10 rad/second. The mechanical properties of interest to step 120 are described below.

With a degree of simplification being understood, when a given stress is applied, as a function of time, upon a viscoelastic material, the corresponding deformation or strain tends to lag the stress function. Accordingly, if the time dependent strain epsilon (t) is a sinusoidal function of time such that:

epsilon (t) = epsilon [m] sin(omega t)

wherein epsilon [m] is the amplitude, t is the time and omega is the angular velocity in radians per unit time, then the corresponding time dependent stress, sigma (t), will also be sinusoidal but will lag by an angle delta such that:

sigma (t)=theta [m]sin (omega t+delta)

When the propellant sample is stressed sinusoidally at a constant angular velocity, G' and G" will be unique functions of time. The parameter G' is termed the storage modulus and G" is termed the loss modulus. The ratio of G"/G' is termed tan delta. Based on the above, it can be seen that the dynamic properties of a propellant can be determined by determining the time dependent functions G', G" and tan delta. In order to get a full definition of these functions by experiment, an inconveniently long time span is required and so a time varying study is impractical. Fortunately, it has been discovered that these time dependent functions have a direct analog in temperature related functions in accordance with the well-known time-temperature Superposition Principle (as discussed, for example, in Rheology, Vol. 2, edited by Frederick R. Eirich, 1958 Academic Press, Inc., N.Y. at p. 67). In the simplest form of this principle, curves of these functions are produced by charting the properties acquired by the Rheometrics mechanical spectrometer.

Returning to FIG. 1, the procedure continues in step 120 as the samples are subjected to small strain dynamic mechanical analysis, and the viscoelastic properties (storage and loss moduli, compliances, tan delta, complex visosity, etc.) are measured over a range of frequencies, and if desired, a range of temperatures. A low strain level (on the order of 1%) is selected to ensure that the tests are nondestructive and the samples can be tested repeatedly throughout the entire aging program. A series of test specimens is aged under controlled temperature and humidity conditions. The mechanical properties of the samples are measured as a function of aging time and aging temperature. A specific measurable parameter (such as complex modulus) is used to determine the overall aging behavior and service life of the propellant.

Step 120 is repeated as the sample fuel is subjected to accelerated aging by heating it to aging temperatures such as those discussed with the present example. From the data collected in step 120, the aging constant K can be calculated in step 150. For this particular fuel, the aging constant is give by $\Delta$log G'/$\Delta$t where:

$\Delta$log G' is the change in the logarithm of the storage modulus measured in step 120; and $\Delta$t is the change in aging time between successive measurements taken in step 120.

The technique of the present invention includes the accelerated aging of propellant samples 130 by storage at elevated temperature as is traditionally conducted within the propulsion community. Service life assessment is made by determining aging rates and activation energies based on the mechanical property degradation of the samples with time over a range of temperatures. The way in which the developed technique differs from traditional methods is that the samples are tested nondestructively, and are tested repeatedly at intervals throughout the aging period. In traditional aging programs samples are tested to failure, so a large amount of material is required for a complete characterization. The techniques described in this application require much fewer samples, much less storage space, and reduced overall handling costs. In addition, samples which have been excised directly from live solid rocket motors can be tested.

Figure 3:
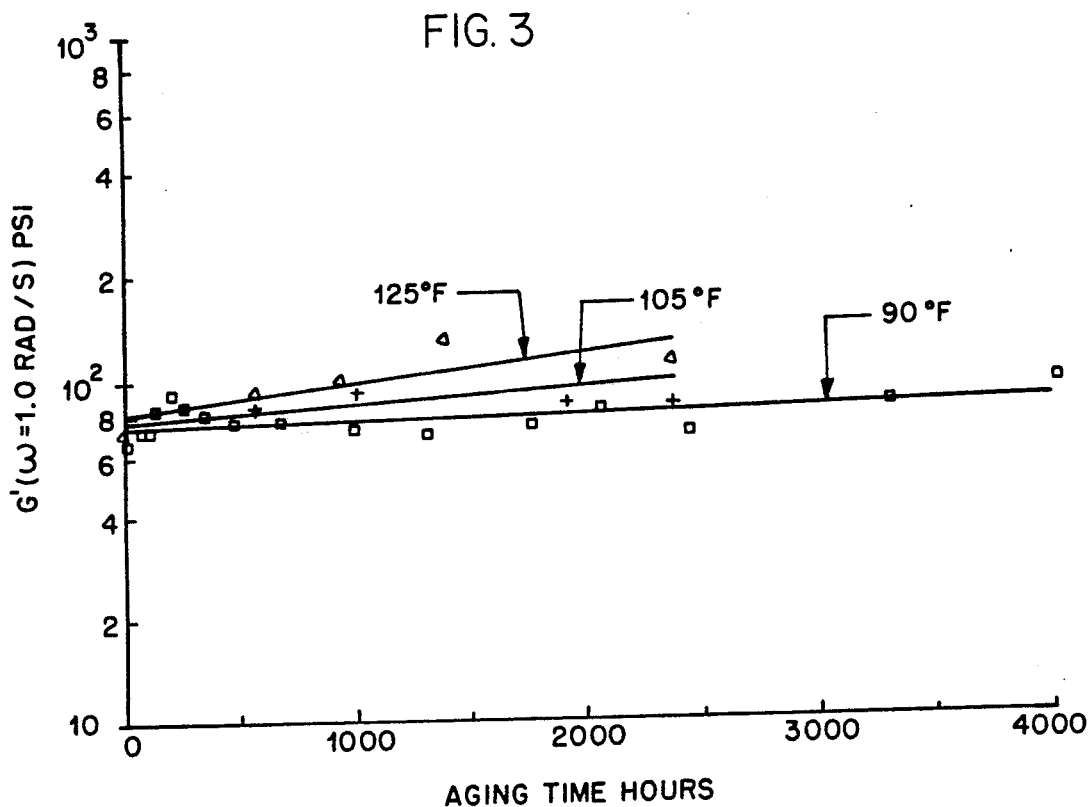
FIG. 3 is a chart of measurements of the storage modulus as a function of age time for MPA motor samples aged at 90° F., 105° F., and 125° F.
Figure 4:
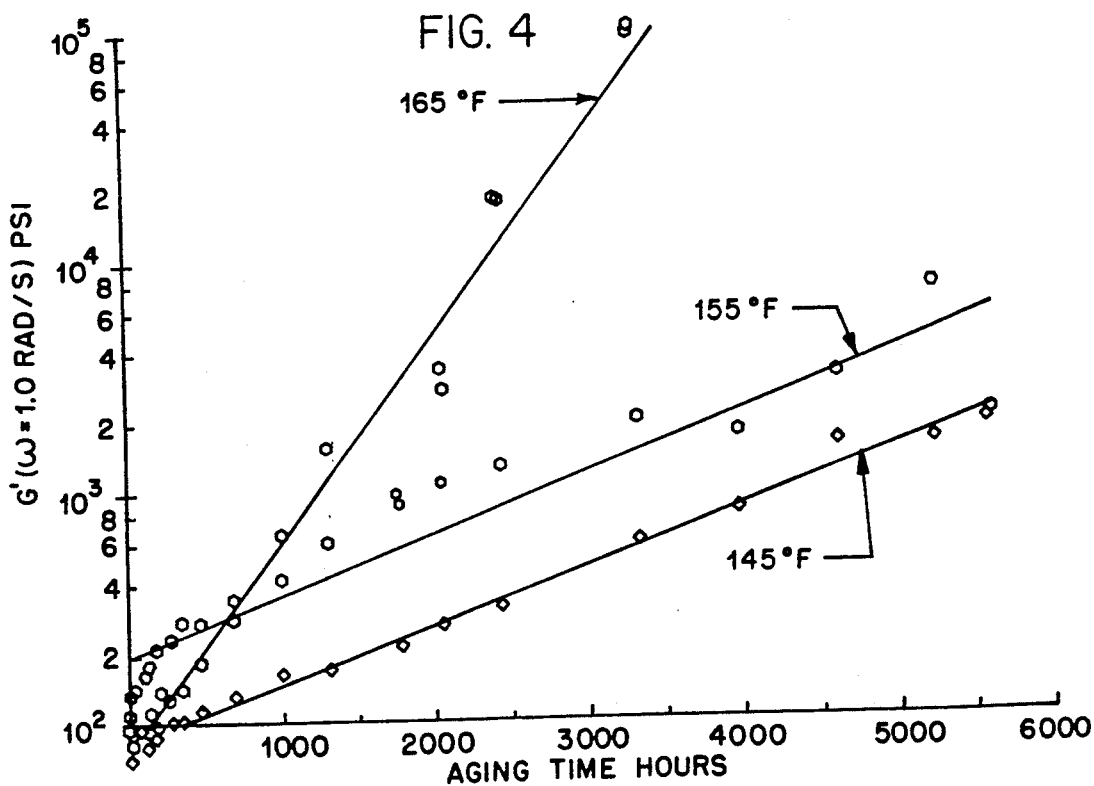
FIG. 4 is a chart of the storage modulus as a function of age time for MPA motor samples aged at 145° F., 155° F. and 165° F.
Figure 5:
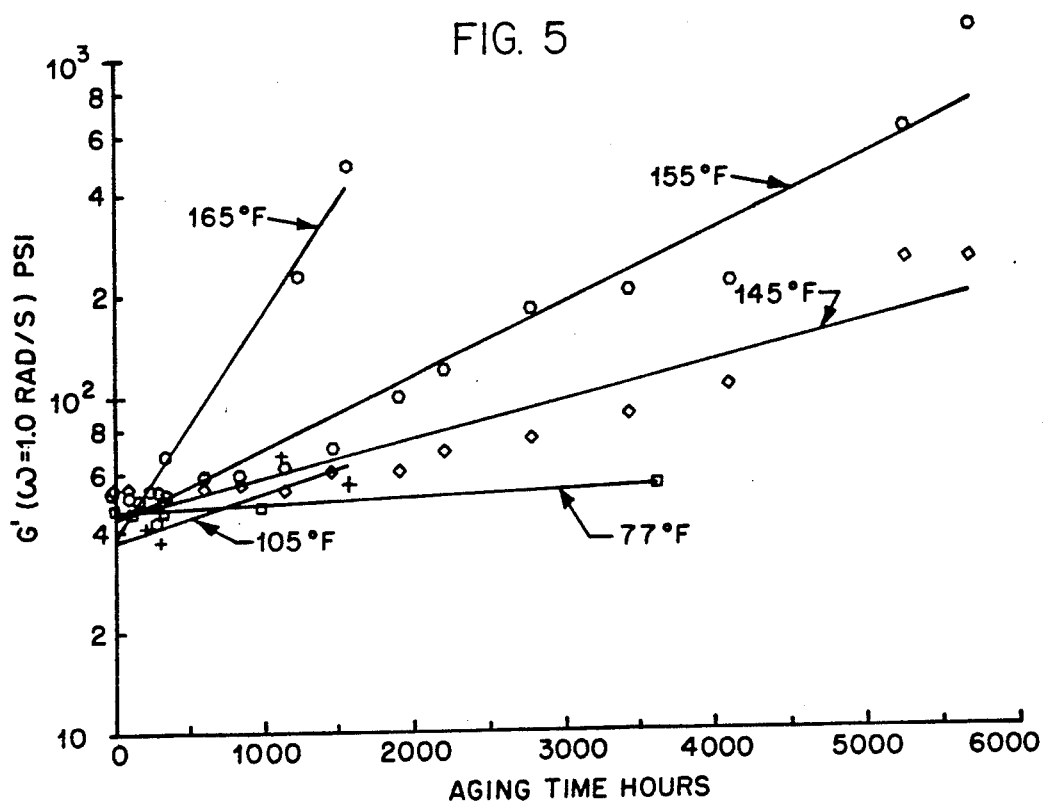
FIG. 5 is a chart of the storage modulus as a function of age time for MPA rectangular samples aged at 77° F., 105° F., 145° F., 155° F. and 165° F.
Figure 6:
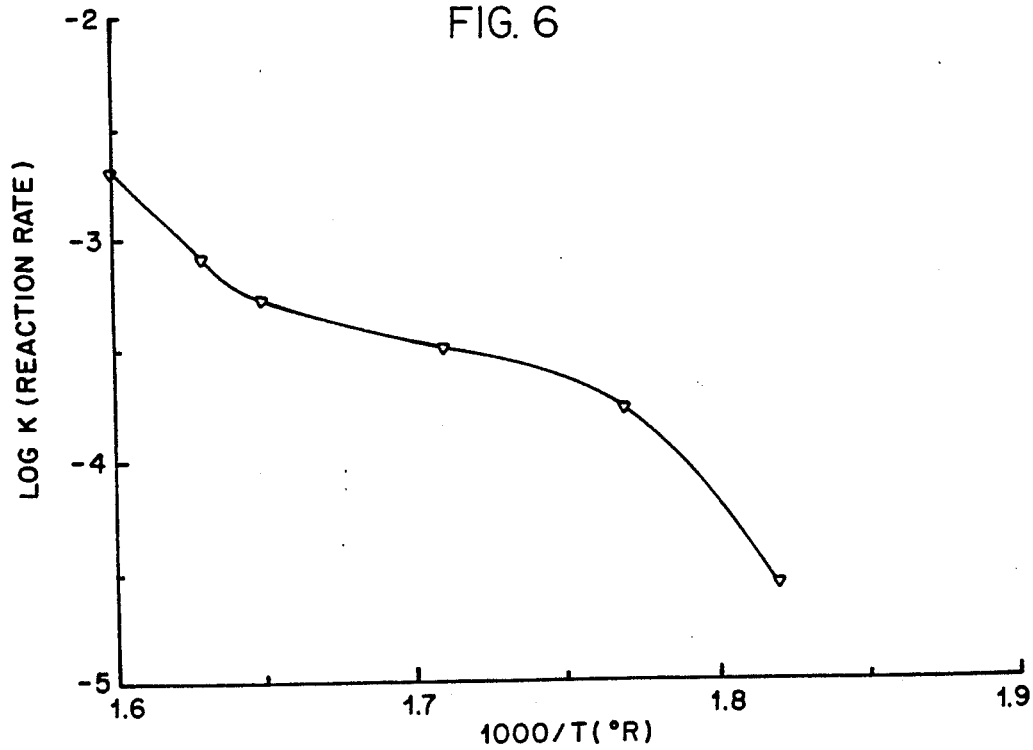
FIG. 6 is a chart of the aging reaction rate constant K as a function of 1000/T for the MPA motor samples.

The technique was developed during a 9-month service life analysis of the propellant in the Maneuver Propulsion Assembly (MPA) motors of a missile. Propellant samples which had been excised directly from MPA motors were aged over a range of temperatures and dynamic mechanical properties were periodically measured. In addition, rectangular propellant samples cut from a slab were subjected to an identical aging analysis, and it was found that the aging behavior of the different type samples was comparable. FIGS. 3 and 4 shows how the storage modulus (G') changes with aging time for motor samples aged at temperatures from 90° to 165° F. An increase in modulus indicates that the material is becoming stiffer, or more brittle. Storage modulus vs. aging time for the rectangular propellant samples is shown in FIG. 5. An Arrhenius analysis of the data confirms that the aging behavior of the rectangular specimens is comparable to that of the samples excised directly from the motor. FIG. 6 shows the rate of aging as a function of temperature for the motor samples. From this plot the aging behavior of the propellant can be determined for any given temperature history between ambient and 165° F. A similar determination of aging behavior using traditional techniques would have required a much larger number of samples.

Returning to FIG. 3, it is noted that the dynamic storage modulus G' of rocket propellant motor samples measurably increases with aging time and aging temperature. This rising modulus indicates that the propellant is becoming more brittle and glass-like as it undergoes the chemical decomposition that can degrade its performance to unacceptable levels. For most solid rocket motor applications, an increase in the propellant modulus by a factor of two to three would result in the end of the motor's useful service life.

Figure 7:
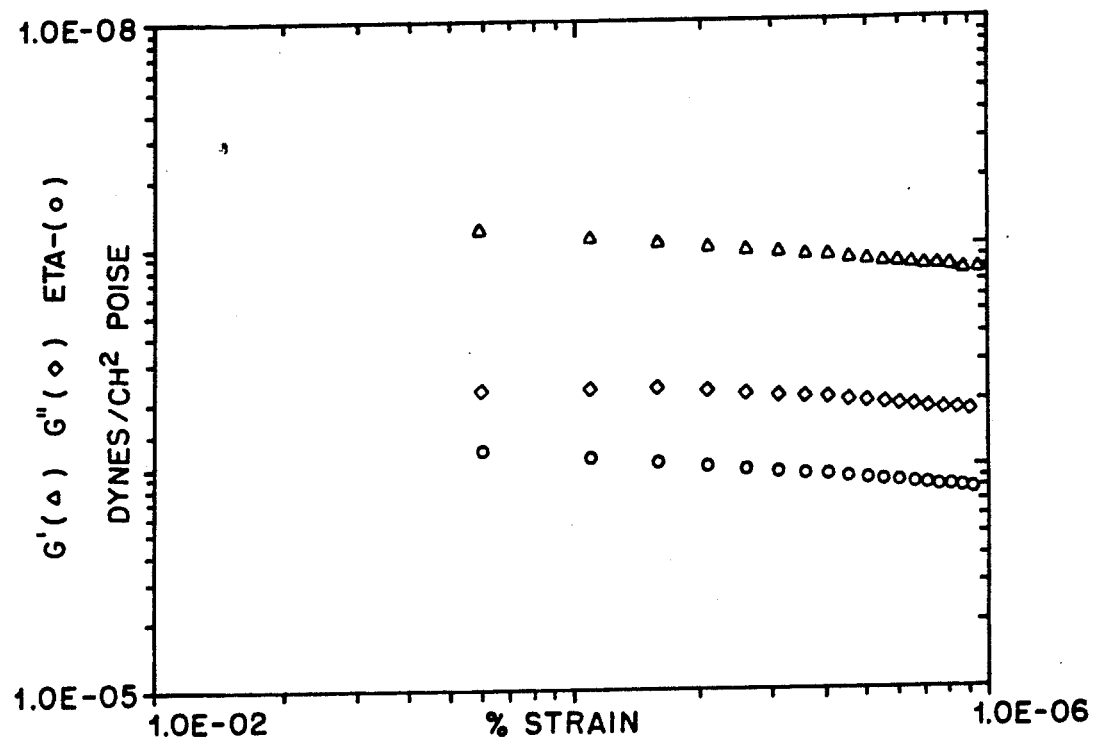
FIG. 7 is a chart of the storage modulus G', the loss modulus G", and the complex viscosity ETA as a function of strain for an MPA motor sample at an oscillation frequency of 10 radions per second.
Figure 8:
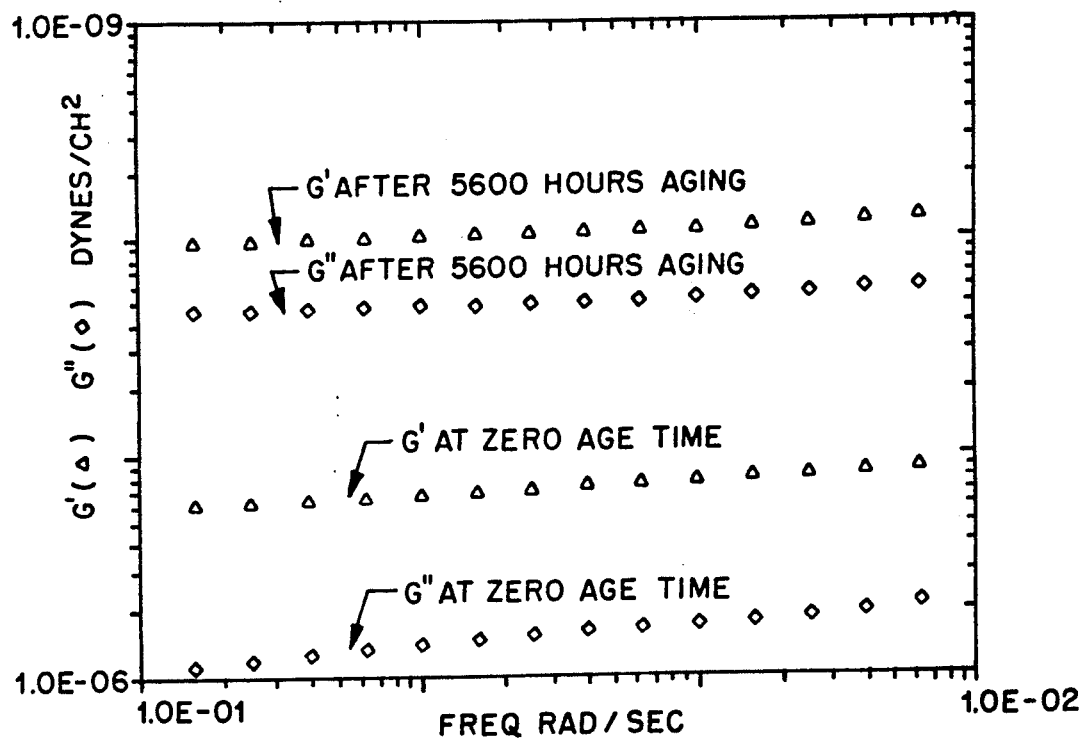
FIG. 8 is a chart of the storage and loss moduli as a function of frequency for an MPA motor sample at zero age time, and after 5,600 hours of aging.

FIG. 7 shows G', G", and $\eta^*$ for MPA motor sample 1 as a function of strain at an oscillation frequency of 10 rad/s. The strain ranges from 0.01% to 1% and the plot reveals that the material approaches the linear viscoelastic region at strain rates approaching 1%. To ensure that the motor samples were not damaged during the measurements, 1% was the maximum strain to which they were subjected. At this strain level, the torque was 20 g-cm or more, a value that is an order of magnitude above the transducer's minimum measurement capability. Based on this information, a strain rate of 1% was selected for the dynamic tests in which the oscillation frequency was varied. FIG. 8 shows the dynamic response as a function of oscillation frequency for MPA motor sample 1 at zero age time and after 5,600 hours of aging at 155° F. Both the storage and loss modulus increased by more than an order of magnitude during this period. Identical frequency sweeps were performed throughout the aging study, and the degradation rate of the mechanical properties was determined for each aging temperature.

Propellant aging data is often analyzed by plotting a measured parameter (such as modulus) vs. the logarithm of age time. Such a plot will linearize the data if the rate of change of the modulus decreases with age time. Using such a method, an aging model based on the Arrhenius form that predicted longtime equivalent aging properties from short-time accelerated aging results, has been developed.

As expected, the dynamic moduli of the MPA propellant samples increased with time and with rising aging temperature. An increase in G', the storage modulus, indicated that the material was becoming more brittle or glasslike. It was found, however, that the modulus was not a function of log time, but instead, increased at a much faster rate. At temperatures from 90° F. to 125° F., the storage modulus of the motor samples was linearly dependent on age time, indicating that the aging rate remained constant over time. FIG. 3 shows the value of the storage modulus at an oscillation frequency of 1.0 rad/s as a function of time for motor samples aged at 90° F., 105° F., and 125° F. The samples shown in this figure are MPA motor sample numbers 9, 12, and 13. The aging rate (rate of increase of G') increased with rising aging temperature, as expected. For temperatures from 145° F. to 165° F., it was found that the logarithm of the storage modulus increased linearly with age time. FIG. 4 shows the storage modulus as a function of age time for motor sample numbers 3, 2, and 8 aged at 145° F., 155° F., and 165° F. respectively. Once again, the aging rate increased with rising aging temperature. A linear relationship between log G' and time means that the aging rate dramatically increased with time. This is a most unusual result, indicating that the longer the propellant is aged, the faster it degrades. The high temperature aging of the MPA propellant was similar to an autocatalytic chemical reaction, whose rate increases with time.

In order to directly compare the aging rates over the entire temperature range from 90° F. to 165° F., the 90° F., 105° F., and 125° F. samples were also plotted as log G' vs. aging time. There is slightly less scatter when the data is plotted in this manner, as shown in FIG. 3. The aging reaction rate constant, k, is equivalent to the slope of these lines. In FIG. 5 the aging data for the torsion rectangular samples are shown. Again, a plot of log G' vs. aging time produces a linear fit of the data. The aging rates also increased with temperature, except at 105° F., for which aging data were only available through 1,500 hours.

The aging rates (slope of the modulus vs. time curves) for all the samples tested are given in Table II. The aging rate constants, k, are equivalent to Δlog G'/Δt. FIGS. 6 shows log k vs. 1/T for the samples, with k determined for each temperature by averaging the k values from each sample at that temperature. This plot shows three general temperature regimes, each with a unique aging rate-temperature dependence. Between 145° F. and 165° F., log k was linearly proportional to 1/T, and the system obeyed the Arrhenius model (Equation 1). In this high temperature region, the activation energy, ΔH, was equal to 50 kcal/mole, which is sufficiently high to indicate that a chemical decomposition occurred at these temperatures. Between 105° F. and 145° F., the reaction rate also fit the Arrhenius equation, but the rate of increase in the aging rate with temperature was much smaller than in the 145° F. to 165° F. temperature range. Below 105° F., the aging rate rapidly decreased with temperature, approaching a zero rate of aging at ambient temperature, which was the lowest temperature examined.

Figure 9:
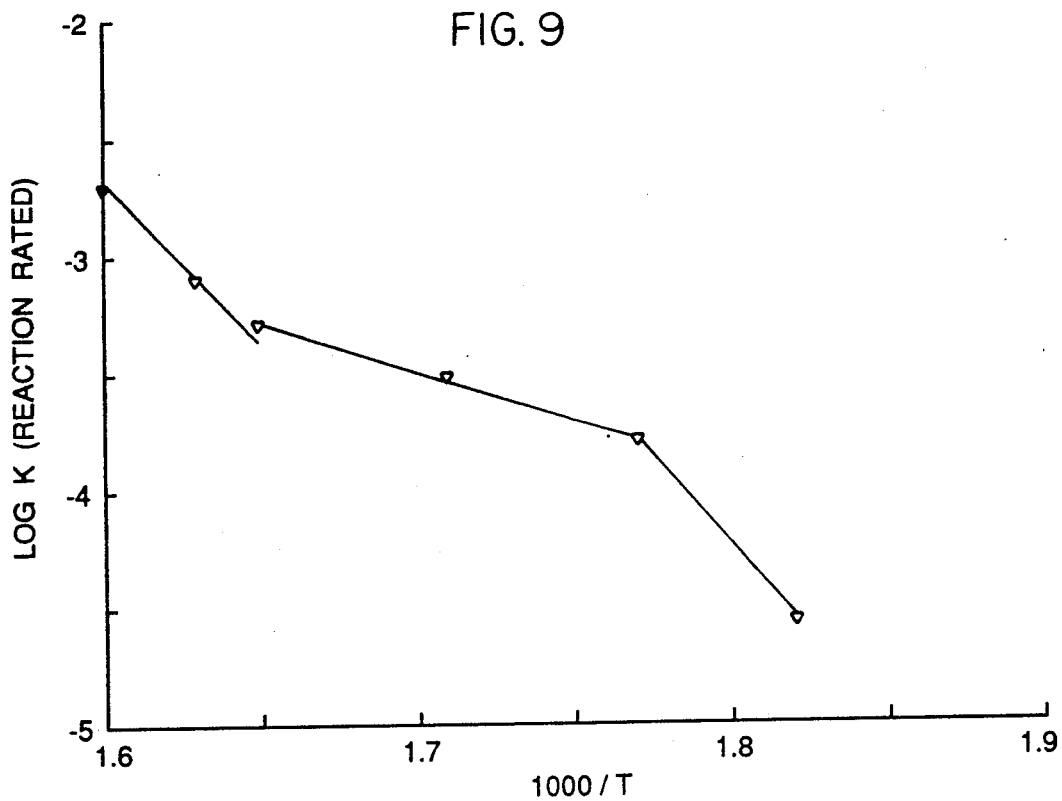
FIG. 9 is a chart of K vs. 1/% for the MPA motor sample showing three temperature regions with distinct aging rate temperature dependence slopes.

It is apparent that at least three different mechanisms were observed in this aging study of the MPA propellant. FIG. 9 shows the log vs 1/T data for the motor samples, with Arrhenius equation fits through each of the distinct temperature regimes. At temperatures close to ambient, the aging processes are either extremely slow or nonexistent. Between 105° F. and 145° F. an Arrhenius model mechanism exists with a moderate increase in aging rate with rising temperature. From 145° F. to 165° F., the aging rate dramatically increases with temperature, indicating that an additional age inducing process was initiated in this range. It is likely that at this high temperature range, the relatively high activation energies of a chemical degradation reaction are achieved.

Figure 10:
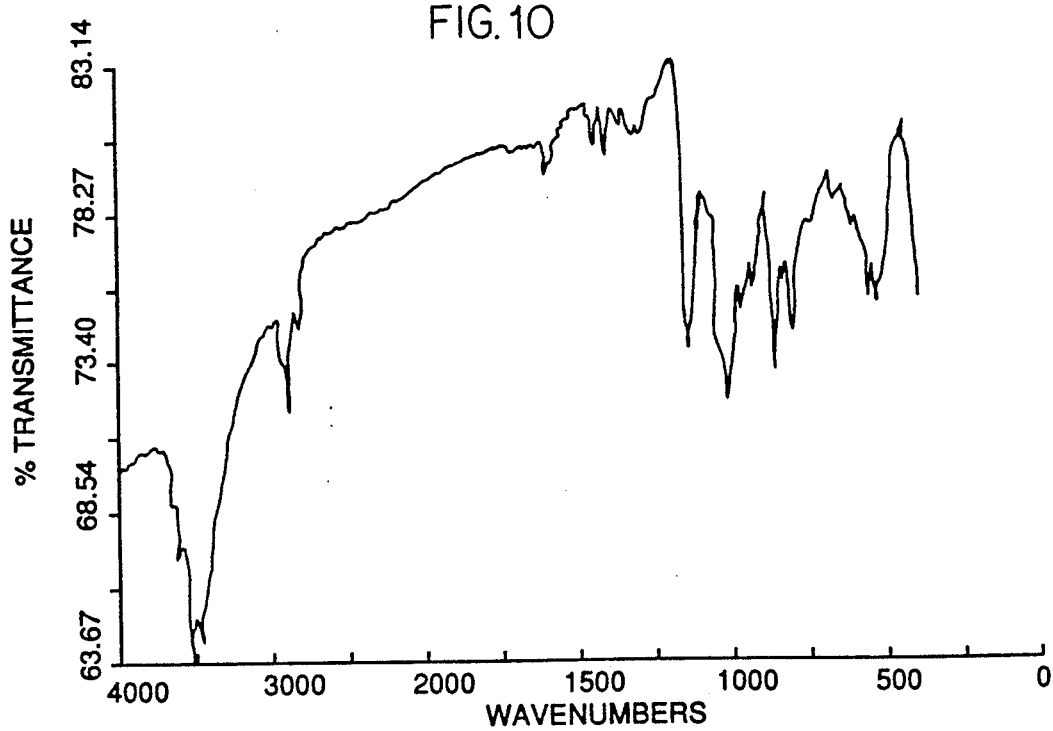
FIG. 10 is a chart of the spectrum of a pure MPA motor sample.
Figure 11:
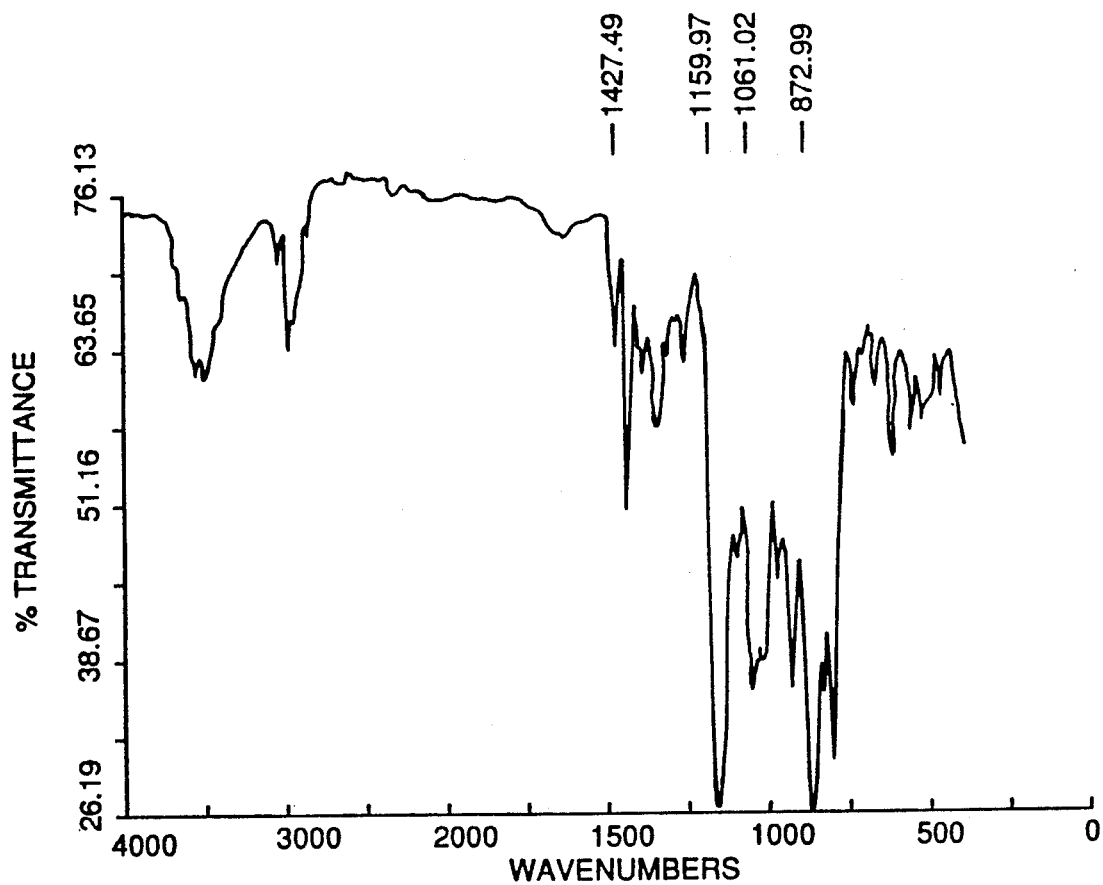
FIG. 11 is a chart of the spectrum of the liquid condensate that volatilized out of the MPA propellant samples.

The volatilization of the plasticizer, TVOPA, from the propellant has been identified as the most likely mechanism contributing to a moderate aging rate (such as exhibited above 105° F.) A clear liquid that condensed onto the parallel plates during the aging process was analyzed by the Fourier Transform Infrared (FTIR) Spectrometer and was confirmed to be TVOPA. FIG. 10 shows the FTIR spectrum of pure TVOPA, while the spectrum of the liquid condensate is shown in FIG. 11. The transmittance peaks of the two materials are virtually identical, verifying that TVOPA volatilized out of the propellant samples during the aging process.

TABLE II

| AGING RATES FOR ALL SAMPLES | | | |
|---|---|---|---|
| Sample No. | Aging Temp. (degree F.) | Aging Rate Constant, k (× 10⁴) | Log( kavg) |
| R* S5 | 77 | 0.435 | −4.36 |
| M** S5 | 90 | 0.243 | |
| MS9 | 90 | 0.300 | −4.57 |
| RS7 | 105 | 3.29 | −3.48 |
| MS12 | 105 | 1.07 | |
| MS15 | 105 | 0.863 | −3.78 |
| MS18 | 105 | 3.08 | |
| MS13 | 125 | 1.92 | |
| MS16 | 125 | 5.49 | −3.50 |
| MS19 | 125 | 2.06 | |
| RS3 | 145 | 2.57 | −3.59 |
| MS3 | 145 | 5.84 | |
| MS7 | 145 | 4.69 | −3.28 |
| RS2 | 155 | 4.95 | −3.31 |
| MS1 | 155 | 5.40 | |
| MS2 | 155 | 6.12 | −3.09 |
| RS6 | 165 | 15.1 | −2.82 |
| MS4 | 165 | 19.2 | |
| MS8 | 165 | 20.7 | −2.70 |

*Rectangular sample 1.5 inches by 0.50 inch by 0.25 inch (cut from slab of propellant).
**Cylindrical motor sample L = 1.0 inch, outer diameter = 0.50 inch, web thickness = 0.10 inch (obtained from MPA motors).

It is believed that the chemical reaction responsible for the rapid rates of aging at high temperatures (above 145° F.) is the decomposition of TVOPA by amines, liberating hydrogen fluoride gas:

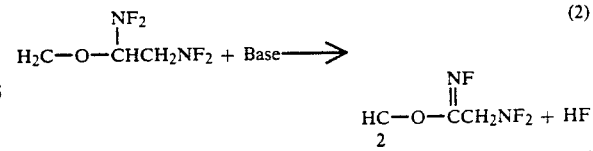

TVOPA can decompose further, liberating two more hydrogen fluoride molecules from each substituted ethoxy group:

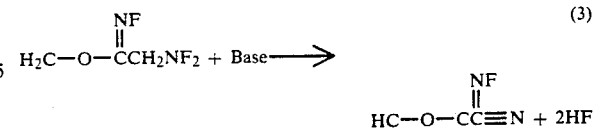

Evidence of decomposition was obtained by placing small propellant samples in sealed test tubes and aging them at 125° F., 145° F. and 165° F. After less than two weeks, the 145° F. and 165° F. samples liberated a gas that clouded the test tubes, and at 165° F., produced dark brown etchings on the inner surface of the test tubes. It is believed this gas was hydrogen fluoride. Over a month of aging at 125° F. produced only trace evidence of this gas.

A comparison of the data listed in Table II reveals that above 145° F. the aging reaction rates are consistently greater for the motor samples than for the rectangular samples. This phenomenon is attributable to the smaller surface area (per unit mass) of the rectangular samples compared with the motor samples. The rate of both of the hypothesized aging mechanisms (volatilization and degradation of TVOPA) is a function of the sample surface area. Thus, the proposed aging mechanisms provided a logical explanation for the difference in aging rates between the motor and rectangular samples.

The measurement of propellant dynamic mechanical properties using a mechanical spectrometer has been found to be a quick, simple, and valuable technique to evaluate propellant age and temperature stability. The test employs a small propellant sample that can be analyzed without destruction of damage, thereby allowing the same sample to be tested repeatedly.

While the invention has been described in its presently preferred embodiment it is understood that the words which have been used are words of description rather than words of limitation and that changes within the purview of the appended claims may be made without departing from the scope and spirit of the invention on its broader aspects.

What is claimed is:

1. A process for determining an age rate for a solid rocket propellant, said process comprising the steps of:
   extracting a sample of said rocket propellant from a rocket motor;
   fixing said sample to test jaws of a mechanical spectrometer;
   subjecting said sample to selected strain levels at a selected frequency;
   measuring dynamic mechanical properties of the solid rocket propellant, said dynamic mechanical properties including a dynamic storage modulus; and
   a step of accelerating aging conditions of said solid rocket propellant after each time said measuring step is performed, said accelerating step including a controlled heating of said solid rocket propellent to temperatures which cause said solid rocket propellant to manifest accelerated aging.

2. A process, as defined in claim 1, wherein said subjecting step is performed at low strain levels which allows the sample to be tested repeatedly with negligible damage occurring.

3. A process, as defined in claim 1, wherein said subjecting step includes an application of said strain levels at the selected frequencies which allows the sample to be tested repeatedly with negligible damage occurring.

4. A process, as defined in claim 1, wherein said extracting step includes a shaping of said sample into a predetermined geometric sample configuration.

5. A process as defined in claim 2, wherein said subjecting step includes an application of said strain levels at the selected frequency which allows the sample to be tested repeatedly with negligible damage occurring.

6. A process, as defined in claim 5, wherein said extracting step includes a shaping of said sample into a predetermined geometric sample configuration.

7. A process for determining an age rate for a solid rocket propellant, said process comprising the steps of:
   extracting a sample of said rocket propellant from a rocket motor;
   shaping said sample into a predetermined geometric sample configuration;
   fixing said sample to test jaws of a mechanical spectrometer;
   subjecting said sample to selected strain levels which allows the sample to be tested repeatedly with negligible damage occurring;
   repeatedly measuring dynamic mechanical properties of the sample of the solid rocket propellant, said dynamic properties including a dynamic storage modulus denoted by $G'$; and
   calculating an aging rate constant indicative of said age rate from successive measurements of said dynamic storage modulus, said calculating step being performed such that $K = \Delta \log G'/\Delta t$ where
   $K$ equals said aging rate constant,
   $\Delta \log G'$ equals a change in a logarithm of successive dynamic storage modulus values, and
   $\Delta t$ equals a change in aging time between successive measurements of said dynamic storage modulus.

8. A process as defined in claim 7, wherein said process includes a step of accelerating aging conditions of said solid rocket propellant after each time said measuring step is performed, said accelerating step including a heating of said solid rocket propellant to temperatures which cause said solid rocket propellant to manifest accelerated aging.

9. A process, as defined in claim 7 wherein said subjecting step includes an application of said strain levels at the selected frequency which allows the sample to be tested repeatedly with negligible damage occurring.

10. A process as defined in claim 9, wherein said solid rocket propellant comprises TVOPA-(1,2,3-Tris 1,2-Bis (Difluoramino Ethoxy) Propane).

11. A process as defined in claim 10, wherein said process includes a step of accelerating aging conditions of said solid rocket propellant after each time said measuring step is performed, said accelerating step including a heating of said solid rocket propellant to temperatures which cause said solid rocket propellant to manifest accelerated aging.

12. A process as defined in claim 11, wherein said accelerating step includes heating said sample to temperatures which may range between 75 and 165 degrees F.

* * * * *